United States Patent [19]

DeLucia

[11] 4,454,605
[45] Jun. 12, 1984

[54] MODULAR X-RAY INSPECTION APPARATUS

[76] Inventor: Victor E. DeLucia, 11846 Mississippi Ave., Los Angeles, Calif. 90025

[21] Appl. No.: 342,610

[22] Filed: Jan. 25, 1982

[51] Int. Cl.$^3$ ............................................. G01N 23/00
[52] U.S. Cl. .................................... 378/57; 250/358.1
[58] Field of Search ............... 250/358.1, 359.1, 360.1; 378/57, 62, 190

[56] References Cited

U.S. PATENT DOCUMENTS

| 3,678,278 | 7/1972 | Peil | 378/57 |
| 4,297,580 | 10/1981 | Juner et al. | 378/57 |
| 4,379,348 | 4/1983 | Haas et al. | 378/57 |

Primary Examiner—Janice A. Howell
Attorney, Agent, or Firm—Keith D. Beecher

[57] ABSTRACT

X-ray apparatus is provided for the inspection of mail, parcels, baggage, and the like, for contraband materials by direct view fluoroscopy. The apparatus is of modular design, in that, it includes a first lead-shielded unit which contains an X-ray fluorescent viewing screen, a mirror, a viewing port for the screen, an inspection compartment, and a door to the inspection compartment; and it also includes a second lead-shielded unit which contains the X-ray generator. The units are mounted in a metal cabinet formed of steel, or other material which need not be lined with heavy lead sheets, or other X-ray impervious material. The first unit is mounted in the upper portion of the cabinet, and the second unit is mounted in the lower portion of the cabinet. X-rays from the second unit are directed through the bottom of the first unit by means of a truncated triangular-shaped guide member formed of X-ray impervious material, such as lead.

5 Claims, 4 Drawing Figures

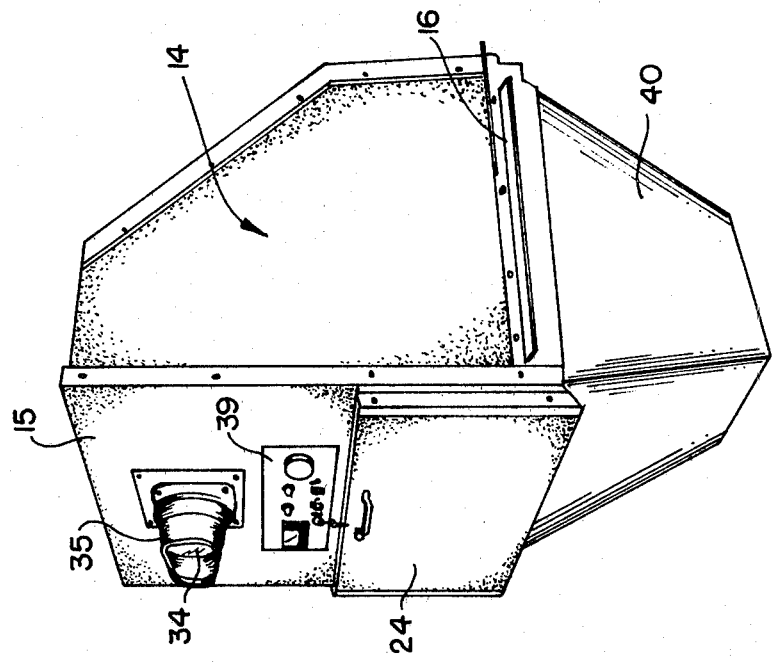
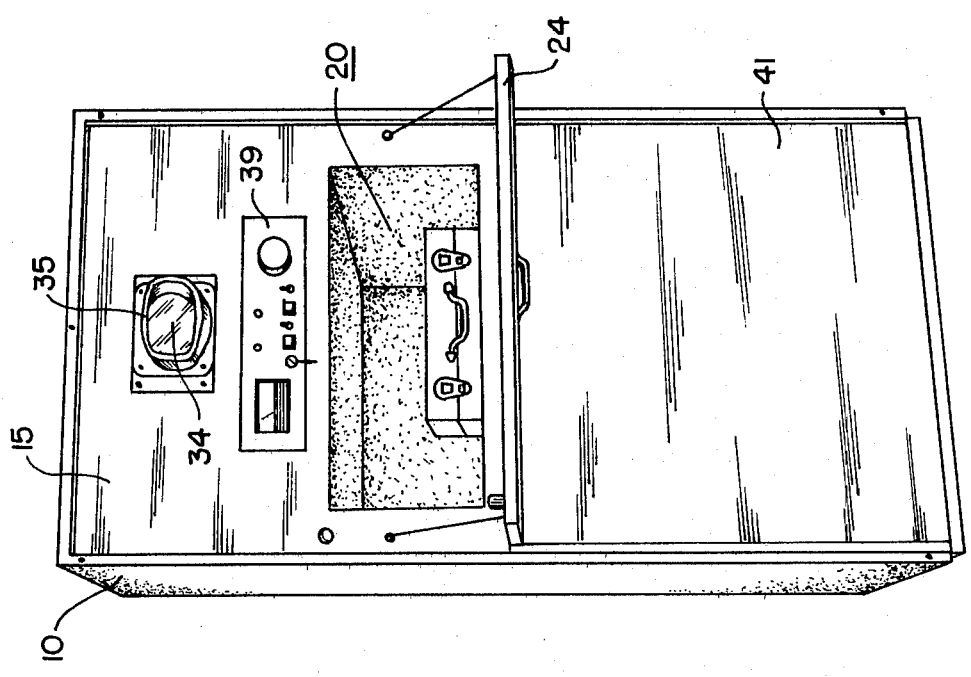

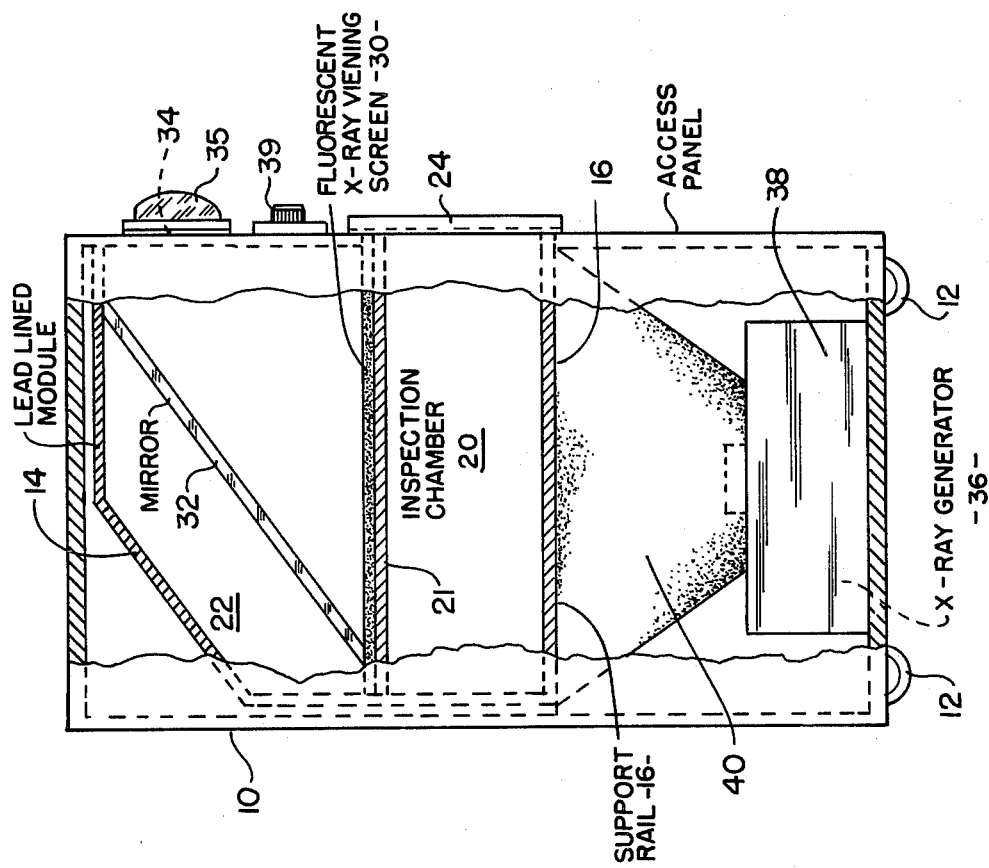
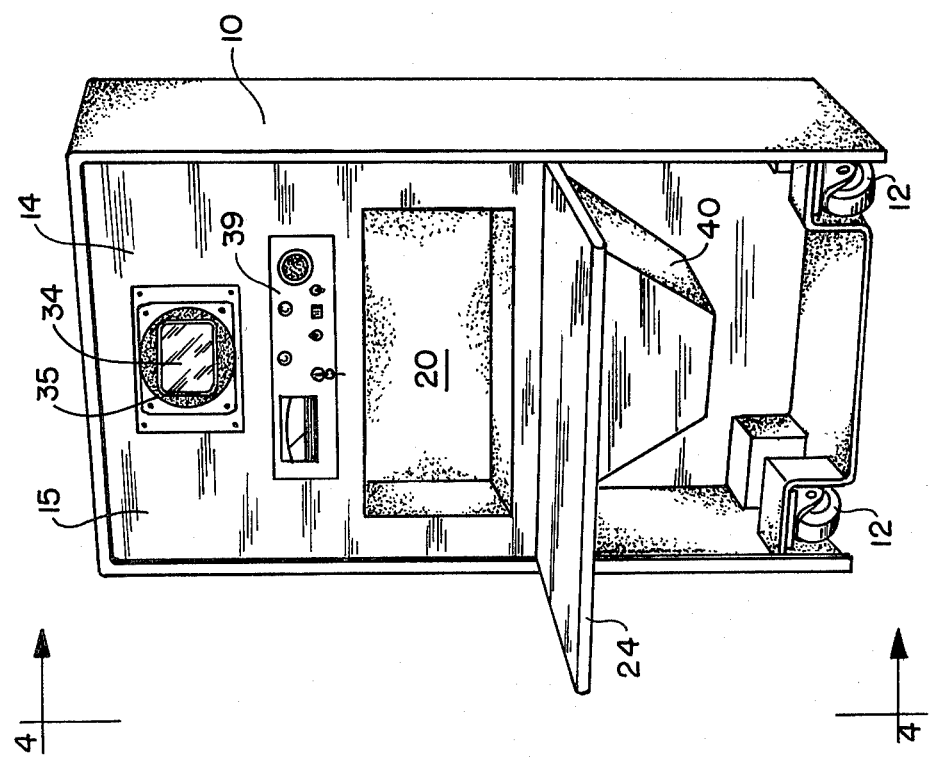

MODULAR X-RAY INSPECTION APPARATUS

BACKGROUND

The use of X-ray systems for baggage and parcel inspection in order to detect contraband has increased considerably in recent years because of terroristic activity which exists at present throughout the world. It is essential that such X-ray inspection equipment be easy to operate, be capable of providing immediate results, and that such equipment does not create any external radiation which could result in X-ray exposure to persons in the vicinity of the equipment.

The X-ray inspection unit of the present invention fulfills all the criteria set forth above. The apparatus of the invention is of the type which finds particular utility in the detection of contraband, and it is intended to be used by governmental, or other agencies, for the inspection of mail, parcels, baggage, and the like, in order to detect weapons, bombs, or other explosives, before the parcels are distributed and opened. One particular use for the apparatus of the invention is in the examination of parcels and food supplies entering a prison. However, it will become evident as the description proceeds, that the apparatus of the invention is of the type having general utility, not only in prisons, but in courtrooms, mailrooms, airports, nuclear sites, and the like.

The X-ray inspection apparatus of the present invention, unlike the prior art X-ray inspection apparatus, is of a modular construction, in that it includes a first lead-shielded modular unit which contains the X-ray viewing screen, mirror, viewing port, inspection compartment and access door; and a second lead-shielded modular unit which contains the X-ray generator. As explained briefly above, the modular units are prefabricated, and they are inserted into a metal cabinet, the cabinet being composed, for example, of steel, or other appropriate material which need not be shielded for X-rays.

One of the advantages of the modular design of the X-ray inspection apparatus of the present invention is that a substantial weight reduction may be achieved, as compared with prior art apparatus of the same general type in which the entire cabinet is shielded for X-rays. For example, in a constructed embodiment of the invention, a weight reduction of 300 pounds has been realized, as contrasted with typical prior art apparatus of comparable power levels. This substantial weight reduction is realized because the lead shielding is used only for the internal modular units, and the cabinet itself need not be shielded.

The modular construction of the apparatus of the invention not only permits a substantial weight reduction, but also permits the cabinet to be constructed to have a clean and attractive appearance, as compared with the bulky machines of the prior art. The substantial weight reduction also provides a considerable saving in shipping costs.

The modular design of the X-ray inspection apparatus of the present invention also obviates any need for access doors in the cabinet, which access doors must be electrically interlocked with the X-ray generator to prevent X-ray exposure when opened, and which interlocks are subject to failure. It is usual for the prior art machines to include at least two such access doors.

Another advantage of the X-ray inspection apparatus of the present invention is that the viewing mirror and fluorescent X-ray viewing screen are contained in a sealed chamber within the first modular unit, and are never exposed to air or dust after the unit has been completed and closed.

As mentioned above, the X-ray generator in the apparatus of the invention is mounted in the second modular unit in the lower portion of the cabinet, and it is readily accessible for removal for maintenance purposes. The removal of the X-ray generator unit from the cabinet is achieved through a removable panel in the cabinet, and there is no need to disturb the unit in any way. Since the X-ray generator itself is enclosed in the second unit, there is no need for the access panel to be shielded, and no need to interlock the panel with the X-ray equipment.

The X-ray inspection apparatus of the invention, in the embodiment to be described, includes a hooded viewing port which is mounted on the front panel of the first modular unit, and through which the fluorescent X-ray viewing screen can be observed, by means of the mirror which is also mounted within the first modular unit. The hood may be removable to permit photographs of the image of the screen to be taken through the viewing port, if so desired.

BRIEF DESCRIPTION OF THE DRAWING

FIG. 1 is a front perspective view of an X-ray inspection unit which is constructed to incorporate the concepts of the present invention;

FIG. 2 is a perspective view of a module which fits into the case of the unit of FIG. 1;

FIG. 3 is a view, like FIG. 1 but with the front access door removed; and

FIG. 4 is a side view, partly in section, to reveal the internal components of the X-ray inspection unit of FIGS. 1 and 3.

DETAILED DESCRIPTION OF THE ILLUSTRATED EMBODIMENT

The X-ray inspection apparatus, as shown in FIGS. 1 and 3, includes a cabinet 10 which may be formed, for example, of steel, or other appropriate material. Cabinet 10 is supported on casters 12 (FIG. 3) which preferably are 360° ballbearing casters, and which are mounted in countersunk sections in the base of the cabinet. This construction shields the caster wheels to improve the physical design of the apparatus, and it eliminates the need for separate heavy angle-iron sub-assemblies to contain the casters.

A lead-shielded module 14 (FIG. 2) is mounted in the cabinet 10, and it is supported in the upper portion of the cabinet on support rails, such as rail 16 (FIGS. 2 and 4). The module 14 is formed or lined with X-ray impervious material, such as lead, with the exception of its bottom. The module has a lead-lined front panel 15.

The module 14 contains an inspection chamber 20 (FIG. 4), and it also contains an upper chamber 22. A door 24 is mounted on the front panel 15 of the module, and which may be opened, as shown in FIGS. 1 and 3, to permit access to the inspection chamber 20, so that articles to be inspected may be inserted into the inspection chamber. The upper chamber 22 is separated from the inspection chamber 20 by an X-ray transmissive panel 21, and a fluorescent X-ray viewing screen 30 is mounted on panel 21. A mirror 32 is positioned in chamber 22 as shown in FIG. 4. The screen 30 may be observed through an observation port 34, which is surrounded by a hood 35. A control panel 39 is also mounted on the front of the unit 14.

An X-ray generator 36 is enclosed in a lead-shielded modular unit 38 (FIG. 4), the modular unit 38 being formed or lined with an X-ray impervious material, such as lead. The unit 38 is mounted in the lower portion of the cabinet. A guide 40 which, likewise, is formed or lined with X-ray impervious material, such as lead, is formed as part of module 14, and it serves to couple the interior of unit 38 to the inspection chamber 20, so that X-rays from the X-ray generator 36 may be directed through the bottom of the unit 14 and through the inspection chamber 20. An access door 41 is mounted on the lower portion of the front of the unit, as shown in FIG. 1, under the panel 15.

In operation of the apparatus, the door 24 is opened, and the article to be inspected is placed in the inspection chamber 20. The X-ray generator 36 is then activated, and X-rays are passed through the inspection chamber 20 by way of guide 40. The X-rays activate the fluorescent X-ray viewing screen 30, so that an impinge of the contents of the package, or the like, in the inspection chamber 20 appear on the screen. The image on the screen is viewed through the viewing port 34, and by way of mirror 32.

The invention provides, therefore, an improved X-ray inspection apparatus which is of a modular construction, and which is constructed so that substantial weight savings, and other advantages may be realized.

It will be appreciated that while a particular embodiment of the invention has been shown and described, modifications may be made, and it is intended in the following claims to cover all modifications which come within the true spirit and scope of the invention.

What is claimed is:

1. X-ray apparatus for the inspection of parcels, mail, baggage, and the like, comprising: a cabinet formed of material transparent to X-rays; a first modular unit mounted in said cabinet shielded with X-ray impervious material and containing an inspection chamber and a further chamber adjacent to said inspection chamber; a door for the inspection chamber mounted on said first modular unit and shielded with X-ray impervious material; a viewing port for the further chamber mounted on said first modular unit; an X-ray viewing screen mounted in said further chamber and observable through said viewing port; a second modular unit mounted in said cabinet shielded with X-ray impervious material; and an X-ray generator mounted in said second modular unit.

2. The X-ray apparatus defined in claim 1, and which includes a mirror mounted in said further chamber in position to enable said X-ray screen to be observed through the viewing port.

3. The X-ray apparatus defined in claim 1, in which said first and second modular units are mounted in said cabinet in spaced relationship, and which includes a guide member shielded with X-ray impervious material coupling said second modular unit to said first modular unit.

4. The X-ray apparatus defined in claim 3, in which said first modular unit is mounted in the upper portion of said cabinet and said second modular unit is mounted in the lower portion of said cabinet, and in which said guide member directs X-rays from said second modular unit upwardly through the bottom of said first modular unit.

5. The X-ray apparatus defined in claim 4, and which includes an access door shielded with X-ray impervious material mounted on the lower portion of the cabinet to permit removal of the second modular unit.

* * * * *